(12) United States Patent
Frantz et al.

(10) Patent No.: US 7,488,707 B2
(45) Date of Patent: Feb. 10, 2009

(54) STRUCTURED SURFACTANT COMPOSITIONS

(75) Inventors: Seren Frantz, Bensalem, PA (US); Stewart Alexander Warburton, West Windsor, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 11/436,914

(22) Filed: May 18, 2006

(65) Prior Publication Data

US 2006/0270584 A1 Nov. 30, 2006

Related U.S. Application Data

(60) Provisional application No. 60/682,965, filed on May 20, 2005.

(51) Int. Cl.
*C11D 1/02* (2006.01)
*C11D 1/72* (2006.01)
*C11D 1/88* (2006.01)
*A61K 8/03* (2006.01)

(52) U.S. Cl. .............. 510/127; 510/155; 510/413; 510/414; 510/421; 510/426; 510/492; 510/505; 510/535; 424/401; 424/70.19; 424/70.24; 424/70.31

(58) Field of Classification Search ........... 510/127, 510/155, 413, 414, 421, 426, 492, 505, 535; 424/401, 70.19, 70.24, 70.31
See application file for complete search history.

(56) References Cited

U.S. PATENT DOCUMENTS

| | | | | |
|---|---|---|---|---|
| 4,964,874 A | 10/1990 | Saphakkul | .................. | 8/429 |
| 5,472,629 A * | 12/1995 | Lysy et al. | .................. | 510/238 |
| 5,556,628 A | 9/1996 | Derian et al. | .................. | 424/401 |
| 5,916,575 A | 6/1999 | McAtee et al. | .................. | 424/401 |
| 5,952,285 A | 9/1999 | Hawkins | .................. | 510/405 |
| 5,952,286 A | 9/1999 | Puvvada et al. | .................. | 510/417 |
| 5,962,395 A | 10/1999 | Puvvada et al. | .................. | 510/418 |
| 6,077,816 A | 6/2000 | Puvvada et al. | .................. | 510/130 |
| 6,150,312 A | 11/2000 | Puvvada et al. | .................. | 510/130 |
| 6,174,846 B1 | 1/2001 | Villa | .................. | 510/159 |
| 6,235,275 B1 | 5/2001 | Chen et al. | .................. | 424/70.1 |
| 6,376,438 B1 | 4/2002 | Rosenberger et al. | .................. | 510/139 |
| 6,426,326 B1 | 7/2002 | Mitra et al. | .................. | 510/130 |
| 6,432,420 B2 | 8/2002 | Ellis et al. | .................. | 424/401 |
| 6,534,456 B2 | 3/2003 | Hayward et al. | .................. | 510/130 |
| 6,534,457 B2 | 3/2003 | Mitra | .................. | 510/130 |
| 6,706,144 B1 | 3/2004 | Furman, Jr. et al. | .................. | 162/72 |
| 6,797,683 B2 | 9/2004 | Shana's et al. | .................. | 510/370 |
| 6,906,015 B1 | 6/2005 | Shiloach et al. | .................. | 510/130 |
| 6,924,256 B2 | 8/2005 | Massaro et al. | .................. | 510/119 |
| 2003/0180246 A1 * | 9/2003 | Frantz et al. | .................. | 424/70.21 |
| 2003/0190302 A1 | 10/2003 | Frantz et al. | .................. | 424/70.24 |
| 2004/0057920 A1 | 3/2004 | Focht et al. | .................. | 424/70.1 |
| 2004/0091446 A1 | 5/2004 | Massaro et al. | .................. | 424/70.21 |
| 2004/0092415 A1 | 5/2004 | Focht et al. | .................. | 510/130 |
| 2004/0219119 A1 | 11/2004 | Wei et al. | .................. | 424/70.1 |
| 2004/0223929 A1 | 11/2004 | Clapp et al. | .................. | 424/63 |
| 2004/0223991 A1 | 11/2004 | Wei et al. | .................. | 424/401 |
| 2004/0223993 A1 | 11/2004 | Clapp et al. | .................. | 424/401 |
| 2004/0234478 A1 | 11/2004 | Clapp et al. | .................. | 424/70.12 |
| 2004/0234565 A1 | 11/2004 | Stell et al. | .................. | 424/401 |
| 2004/0235693 A1 | 11/2004 | Wei et al. | .................. | 510/130 |
| 2004/0235702 A1 | 11/2004 | Hawkins | .................. | 510/417 |
| 2004/0248748 A1 | 12/2004 | Wei et al. | .................. | 510/130 |
| 2005/0020468 A1 | 1/2005 | Frantz et al. | .................. | 510/424 |
| 2005/0100570 A1 | 5/2005 | Wei et al. | .................. | 424/401 |
| 2005/0143268 A1 | 6/2005 | Midha et al. | .................. | 510/130 |
| 2005/0143269 A1 | 6/2005 | Wei et al. | .................. | 510/130 |
| 2005/0153852 A1 | 7/2005 | Evans et al. | .................. | 510/130 |
| 2005/0170979 A1 | 8/2005 | Massaro et al. | .................. | 510/130 |
| 2005/0175568 A1 | 8/2005 | Asari et al. | .................. | 424/70.12 |
| 2005/0192187 A1 | 9/2005 | Wagner et al. | .................. | 510/130 |
| 2005/0192188 A1 | 9/2005 | Wagner et al. | .................. | 510/130 |
| 2005/0192189 A1 | 9/2005 | Wagner et al. | .................. | 510/130 |
| 2005/0233917 A1 | 10/2005 | Shiloach et al. | .................. | 510/130 |
| 2005/0233935 A1 * | 10/2005 | Gunn et al. | .................. | 510/418 |
| 2005/0238595 A1 | 10/2005 | Stell et al. | .................. | 424/130 |
| 2005/0239670 A1 | 10/2005 | Stella et al. | .................. | 510/130 |
| 2005/0276768 A1 | 12/2005 | Wei et al. | .................. | 424/63 |
| 2005/0276829 A1 | 12/2005 | Stella et al. | .................. | 424/401 |
| 2006/0008438 A1 | 1/2006 | Velarde et al. | .................. | 424/70.12 |
| 2006/0040837 A1 | 2/2006 | Frantz et al. | .................. | 510/417 |
| 2006/0183662 A1 | 8/2006 | Crotty et al. | .................. | 510/499 |
| 2006/0234886 A1 | 10/2006 | Massaro et al. | .................. | 510/130 |
| 2006/0270563 A1 | 11/2006 | Yang et al. | .................. | 507/417 |
| 2006/0270584 A1 | 11/2006 | Frantz et al. | .................. | 510/417 |
| 2007/0027050 A1 | 2/2007 | Crotty et al. | .................. | 510/130 |

* cited by examiner

*Primary Examiner*—Brian P Mruk

(57) ABSTRACT

An aqueous structured surfactant composition, contains water, one or more anionic surfactants, and one or more alkoxylated nonionic surfactants, wherein at least one alkoxyl unit per molecule of the alkoxylated nonionic surfactants is a propoxyl unit or a butoxyl unit, exhibits shear-thinning viscosity, is capable of suspending water insoluble or partially water soluble components, and is mild to the eyes and skin.

18 Claims, No Drawings

STRUCTURED SURFACTANT COMPOSITIONS

This application claims benefit of Provisional Application 60/682,965, filed May 20, 2005

FIELD OF THE INVENTION

This invention relates to surfactant compositions, more particularly to structured surfactant systems.

BACKGROUND OF THE INVENTION

Structured surfactant compositions are pumpable compositions that exhibit shear-thinning viscosity and have the capacity physically to suspend water insoluble or partially water soluble ingredients. In many cases, the surfactant is present in such structured surfactant compositions in the form of packed spherulites, i.e., lamellar droplets, formed from an aqueous solution of the surfactant.

Structured surfactant compositions are useful in personal care applications, such as shampoos, body wash, hand soap, lotions, creams, conditioners, shaving products, facial washes, neutralizing shampoos, and skin treatments, in home care applications, such as liquid detergents, laundry detergents, hard surface cleansers, dish wash liquids, toilet bowl cleaners, and in other applications, such as oil field and agrochemical applications.

In some personal care compositions, such as, for example, children's shampoos, it important that the composition not irritate the eyes. In other applications, such as facial washes and compositions for sensitive skin, it is important that the composition does not irritate the skin. Ethoxylated nonionic surfactants, typically one or more ethoxylated alcohols or ethoxylated sorbitan esters, are typically used in such compositions because such ethoxylated nonionic surfactants are mild to the eyes and skin. However, higher (for example, with 3 or more ethylene oxide units per molecule) ethoxylated alcohols and ethoxylated sorbitan esters tend to be incompatible with structured surfactant systems in that such compounds tend to destroy the structure of such systems.

What is needed is a structured surfactant composition that provides typical structured surfactant properties, that is, shear-thinning viscosity and a capacity to suspend water insoluble or partially water soluble components and is mild to the skin and/or eyes.

SUMMARY OF THE INVENTION

In a first aspect, the present invention is directed to an aqueous structured surfactant composition, comprising water, one or more anionic surfactants, and at least one alkoxylated nonionic surfactant, wherein at least one alkoxyl unit per molecule of such alkoxylated nonionic surfactant is a propoxyl unit or a butoxyl unit, said composition exhibiting shear-thinning viscosity and is capable of suspending water insoluble or partially water soluble components.

In a second aspect, the present invention is directed to a surfactant blend, comprising, based on 100 parts by weight ("pbw") of the blend, from 3 pbw to 40 pbw of one or more anionic surfactants, and from greater than 0 pbw to 40 pbw of at least one alkoxylated nonionic surfactant, wherein at least one alkoxyl unit per molecule of such alkoxylated nonionic surfactant is a propoxyl unit or a butoxyl unit.

In a third aspect, the present invention is directed to a personal care composition comprising water, one or more anionic surfactants, and at least one alkoxylated nonionic surfactant, wherein at least one alkoxyl unit per molecule of such alkoxylated nonionic surfactant is a propoxyl unit or a butoxyl unit, said composition exhibiting shear-thinning viscosity and is capable of suspending water insoluble or partially water soluble components.

The personal care composition of the present invention exhibits structured surfactant properties, that is, shear-thinning viscosity and a capacity to suspend water insoluble or partially water soluble components and is mild to the eyes and/or skin.

DETAILED DESCRIPTION OF INVENTION AND PREFERRED EMBODIMENTS

As used herein in reference to viscosity, the terminology "shear-thinning" means that such viscosity decreases with an increase in shear rate. Shear-thinning may be characterized as a "non-Newtonian" behavior, in that it differs from that of a classical Newtonian fluid, for example, water, in which viscosity is not dependent on shear rate.

As used herein in reference to a component of an aqueous composition, the terminology "water insoluble or partially water soluble components" means that the component is present in the aqueous composition at a concentration above the solubility limit of the component so that, in the case of a water insoluble component, the component remains substantially non-dissolved in the aqueous composition and, in the case of a partially water soluble component, at least a portion of such component remains undissolved in the aqueous composition.

As used herein, characterization of an aqueous composition as "capable of suspending", or as being "able of suspend" water insoluble or partially water insoluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition.

In one embodiment, the structured surfactant composition comprises at least one lamellar phase, said lamellar phase comprising water, at least a portion of the anionic surfactant and at least a portion of the alkoxylated nonionic surfactant.

As used herein, the terminology "lamellar phase" means a phase that comprises a plurality of bilayers of surfactant arranged in parallel and separated by liquid medium. A lamellar phase is detectable by, for example, small angle x-ray measurement or by evidence of birefringence under a cross-polarized microscope. Lamellar phases include both spherulitic phases and the typical form of the liquid crystal G-phase, as well as mixtures thereof. "G-phases", which are sometimes referred to in the literature a $L_\alpha$ phases, are typically pumpable, non-Newtonian, anisotropic products that are cloudy looking and exhibit a characteristic "smeary" appearance on flowing. Lamellar phases, can exist in several different forms, including domains of parallel sheets which constitute the bulk of the typical G-phases described above and spherulites formed from a number of concentric spheroidal shells, each of which is a bilayer of surfactant. In this specification the term "G-phase" will be reserved for compositions which are at least partly of the former type. The spherulites are typically between 0.1 and 50 microns in diameter and so differ fundamentally from micelles. Unlike micellar solutions, spherulitic compositions are typically anisotropic and non-Newtonian. When close packed, spherulites have good solid suspending properties and allow incorporation of water insoluble or partially water soluble solids, liquids and/or gases as a separate, discontinuous phase suspended in a continuous matrix of the surfactant composition.

As used herein, the term "alkyl" means a saturated straight chain, branched chain, or cyclic hydrocarbon radical, such as for example, methyl, ethyl, n-propyl, iso-propyl, n-butyl, sec-butyl, t-butyl, pentyl, n-hexyl, cyclohexyl.

As used herein, the term "alkenyl" means an unsaturated straight chain, branched chain, or cyclic hydrocarbon radical having at least one carbon-carbon double bond per radical, such as for example, propenyl, butenyl.

As used herein, the term "alkynyl" means an unsaturated straight chain, branched chain, or cyclic hydrocarbon radical having at least one carbon-carbon triple bond per radical, such as for example, propynyl, butynyl.

As used herein, the term "alkoxyl" means a saturated or unsaturated straight chain or branched chain ether radical, such as for example, ethoxy, propoxy, isopropoxy, butoxy, the term "alkoxylated" or "alkoxylate" in reference to an organic moiety means that the moiety is substituted with one or more alkoxy groups, typically with a polyether group, such as, for example a poly(ethoxy), poly(propoxy) or poly(ethoxypropoxy) group, the term "propoxylated" in reference to an organic moiety means that the moiety is substituted with a at least one propoxyl unit, and the term "butoxylated" in reference to an organic moiety means that the moiety is substituted with at least one butoxyl unit. As used herein, the notation "(n)", wherein n is an integer, in reference to the polyalkoxy group of an alkoxylated moiety indicates the number of alkoxy units in the polyalkoxy group. For example, "propoxylated (5) decyl alcohol" means decyl alcohol alkoxylated with 5 moles of propoxyl units per mole of decyl alcohol and butoxylated (3) dodecyl alcohol means decyl alcohol alkoxylated with 3 moles of butoxyl units per mole of decyl alcohol.

As used herein, the terminology "($C_n$-$C_m$)" in reference to an organic group, wherein n and m are each integers, indicates that the group may contain from n carbon atoms to m carbon atoms per group.

As used herein, the terminology "alcohols" refers to saturated or unsaturated fatty alcohols, typically ($C_8$-$C_{24}$)alcohols, such as, for example, hexyl alcohol, ocyl alcohol, decyl alcohol, undecyl alcohol, dodecyl alcohol, tridecyl alcohol, pentadecyl alcohol, hexadecyl alcohol, heptadecyl alcohol, octadecyl alcohol, nonadecyl alcohol, eicosyl alcohol, ducosyl alcohol, tricosyl alcohol, as well as mixtures thereof.

In one embodiment, the composition of the present invention comprises, based on 100 pbw of the composition, from about 10 to about 80 pbw, more typically from about 20 to about 70 pbw, even more typically from about 30 to about 60 pbw, still more typically from about 25 about 55 pbw, and most typically from about 35 to about 50 pbw, water.

In one embodiment, the structured surfactant composition of the present invention comprises from about 3 to about 40 pbw, more typically from about 5 to about 30 pbw, and still more typically from about 8 to about 20 pbw, of the one or more anionic surfactants.

Anionic surfactants are known. Any anionic surfactant that is acceptable for use in the intended end use application is suitable as the anionic surfactant component of the composition of the present invention, including, for example, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl(ether)phosphates, dialkyl (ether)phosphates, sarcosinates, sulfosuccinates, isethionates, and taurates, as well as mixtures thereof. Commonly used anionic surfactants that are suitable as the anionic surfactant component of the composition of the present invention include, for example, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl phosphate, sodium tridecyl phosphate, sodium behenyl phosphate, sodium laureth-2 phosphate, sodium ceteth-3 phosphate, sodium trideceth-4 phosphate, sodium dilauryl phosphate, sodium ditridecyl phosphate, sodium ditrideceth-6 phsphate, sodium lauroyl sarcosinate, lauroyl sarcosine, cocoyl sarcosine, ammonium cocyl sulfate, ammonium lauryl sulfate, sodium cocyl sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium lauryl sulfate, potassium cocyl sulfate, potassium lauryl sulfate, monoethanolamine cocyl sulfate, sodium tridecyl benzene sulfonate, and sodium dodecyl benzene sulfonate. Branched anionic surfactants are particularly preferred, such as sodium trideceth sulfate, sodium tridecyl sulfate, ammonium trideceth sulfate, ammonium tridecyl sulfate, and sodium trideceth carboxylate.

The cation of any anionic surfactant is typically sodium but may alternatively be potassium, lithium, calcium, magnesium, ammonium, or an alkyl ammonium having up to 6 aliphatic carbon atoms including isopropylammonium, monoethanolammonium, diethanolammonium, and triethanolammonium. Ammonium and ethanolammonium salts are generally more soluble that the sodium salts. Mixtures of the above cations may be used.

In one embodiment, the composition of the present invention comprises, based on 100 pbw of the composition, from about 10 to about 80 pbw, more typically from about 20 to about 70 pbw, even more typically from about 30 to about 60 pbw, still more typically from about 25 about 55 pbw, and most typically from about 35 to about 50 pbw, water.

In one embodiment, the structured surfactant composition of the present invention comprises from about 3 to about 40 pbw, more typically from about 5 to about 30 pbw, and still more typically from about 8 to about 20 pbw, of the one or more anionic surfactants.

Suitable alkoxylated nonionic surfactants include alkoxylated alcohols, alkoxylated alkanolamides, alkoxylated fatty acids, and alkoxylated sorbitan derivatives and comprise from 1 mole to about 200 moles, more typically from 1 mole to about 100 moles, of ($C_2$-$C_4$)alkylene oxide units per mole of alkoxylated nonionic surfactant, wherein, on average, at least one alkoxyl unit per molecule of alkoxylated nonionic surfactant is a propoxyl unit. More typically, based on the total number of alkoxyl units of the alkoxylated nonionic surfactant, greater than 30%, more typically greater than 50%, even more typically greater than 80%,and still more typically greater than 99% of the alkoxyl units of the alkoxylated nonionic surfactant are propoxyl units.

The subcategories defined above, that is, alkoxylated alcohols, alkoxylated alkanolamides, alkoxylated fatty acids, and alkoxylated sorbitans, are convenient, but not rigorously distinct. Certain compounds, such as, for example, a propoxylated sorbitan laurate, may contain more than one of the functional groups used to define the subcategories. As referred to herein, such compounds are subcategorized based on the following hierarchy: sorbitan>carboxylic acid>amide>alcohol. For example, an alkoxylated compound, such as a propoxylated sorbitan laurate, that is derived from sorbitan and further contains a hydroxyl and/or a carboxylic acid functional group is subcategorized herein as an alkoxylated sorbitan, an alkoxylated compound, such as a propoxylated stearic acid monoester, that is not derived from sorbitan, is derived from a carboxylic acid, and further contains a hydroxyl group is subcategorized herein as an alkoxylated carboxylic acid, and an alkoxylated compound, such as a propoxylated hexadecyl alcohol, that is not derived from sorbitan, is not derived from a carboxylic acid, and contains a hydroxyl group is subcategorized herein as an alkoxylated alcohol.

Suitable alkoxylated alcohols include compounds corresponding to those obtained by conceptually substituting a group according to formula (I):

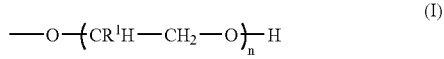

wherein:
each $R^1$ is independently H, methyl, or ethyl, provided that at least one $R^1$ per molecule is methyl or ethyl, and
n is an integer of from about 1 to about 200, more typically from about 2 to about 100, and still more typically from about 4 to about 30, and most typically from about 6 to about 20, for one or more hydroxyl groups of an alcohol, and include, for example, for example, propoxylated (1) ocyl alcohol, propoxylated (2) decyl alcohol, propoxylated (2) undecyl alcohol, propoxylated (3) dodecyl alcohol, butoxylated (3) dodecyl alcohol, propoxylated (4) tridecyl alcohol, propoxylated (12) pentadecyl alcohol, propoxylated (18) hexadecyl alcohol, propoxylated (5) heptadecyl alcohol, propoxylated (15) octadecyl alcohol, propoxylated (18) nonadecyl alcohol, propoxylated (10) eicosyl alcohol, butoxylated (10) eicosyl alcohol, propoxylated (10) cetyl alcohol, propoxylated (12) ducosyl alcohol, propoxylated (15) tricosyl alcohol, and mixtures thereof.

Typically, greater than 30%, more typically greater than 50%, still more typically greater than 80%, and most typically greater than 99% of the $R^1$ groups per molecule are each independently methyl or ethyl, based on the total number of moles of $R^1$ groups per molecule. In one embodiment, each $R^1$ is independently methyl or ethyl, more typically methyl.

In one embodiment, the alkoxylated nonionic surfactant comprises at least one alkoxylated alcohol according to formula (II):

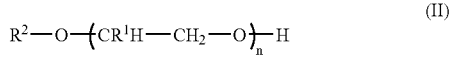

wherein $R^2$ is alkyl, alkenyl, or alkynyl, more typically ($C_8$-$C_{24}$)alkyl or ($C_8$-$C_{24}$alkenyl, and $R^1$ and n are each as described above.

More typically, $R^1$ is methyl, $R^2$ is ($C_{12}$-$C_{20}$)alkyl and n is from 1 to about 200, more typically from about 2 to about 100, and still more typically from about 4 to about 30, and most typically from about 6 to about 20.

Suitable alkoxylated alkanolamides include compounds corresponding to those obtained by conceptually substituting a group according to the formula (III):

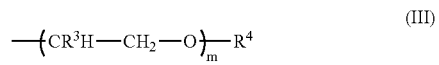

wherein:
each $R^3$ is independently H, methyl, or ethyl, provided that at least one $R^3$ per molecule is methyl or ethyl,
$R^4$ is H, and
m is an integer of from 1 to about 200, for one or more hydroxyl groups of an alkanolamide and include, for example, propoxylated (2)coco monoethanolamide, butoxylated (5) coco monoisopropanolamide, and propoxylated (5) coco monoisopropanolamide.

Typically, greater than 30%, more typically greater than 50%, still more typically greater than 80%, and most typically greater than 99% of the $R^3$ groups per molecule are each independently methyl or ethyl, based on the total number of moles of $R^3$ groups per molecule. In one embodiment, each $R^3$ is independently methyl or ethyl, more typically methyl.

In one embodiment, the alkoxylated nonionic surfactant comprises at least one alkoxylated alkanolamide according the structural formula (IV):

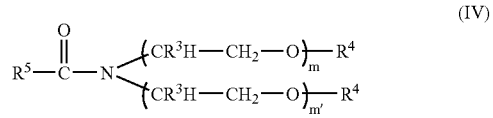

wherein:
$R^3$, $R^4$, and m are each as described above,
$R^5$ is alkyl, alkenyl, or alkynyl, more typically ($C_8$-$C_{24}$) alkyl or ($C_8$-$C_{24}$alkenyl,
m' is 0 or an integer of from 1 to about 200, and
if m' is not 0, then the sum of m+m' is from 2 to about 200.
More typically, $R^3$ is methyl, $R^5$ is ($C_{12}$-$C_{20}$) alkyl, m is from 1 to about 100, more typically from 1 to about 30, and m' is from 1 to about 100, more typically from 1 to about 30, or is 0.

Suitable alkoxylated fatty acids include compounds corresponding to those obtained by conceptually substituting a group according to formula (V):

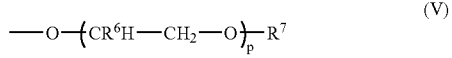

wherein
each $R^6$ is independently H, methyl, or ethyl, provided that at least one $R^8$ per molecule is methyl or ethyl,
$R^7$ is independently H, alkyl, alkenyl, or alkynyl or

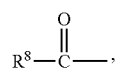

$R^8$ is alkyl, alkenyl, or alkynyl, more typically ($C_8$-$C_{24}$) alkyl or ($C_8$-$C_{24}$alkenyl, and
p is an integer of from 1 to about 200, for one or more hydroxyl groups of a fatty acid and include, for example, propoxylated esters of ($C_{10}$-$C_{22}$) saturated or unsaturated carboxylic acids, for example, propoxylated (10) propylene glycol isostearate, butoxylated (10) propylene glycol isostearate, propoxylated (3) propylene glycol oleate, propoxylated (5) glyceryl isostearate, propoxylated (8) glyceryl oleate, butoxylated (8) glyceryl oleate.

Typically, greater than 30%, more typically greater than 50%, still more typically greater than 80%, and most typically greater than 99% of the $R^6$ groups per molecule are each independently methyl or ethyl, based on the total number of moles of $R^6$ groups per molecule. In one embodiment, each $R^6$ is independently methyl or ethyl, more typically methyl.

In one embodiment, the alkoxylated nonionic surfactant comprises at least one alkoxylated fatty acid according the structural formula (VI)

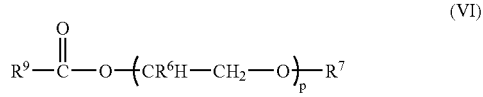

(VI)

wherein:
each $R^9$ is independently alkyl, alkenyl, or alkynyl, more typically
($C_8$-$C_{24}$) alkyl or ($C_8$-$C_{24}$ alkenyl, and
$R^6$, $R^7$, and p are each as described as above.
More typically, $R^6$ is methyl, $R^7$ is H, $R^9$ is $C_{12}$-$C_{20}$, and p is from 2 to about 20.

Suitable alkoxylated sorbitan derivatives include compounds corresponding to those obtained by conceptually substituting a group according the formula (VII),

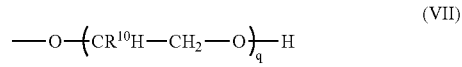

(VII)

wherein
each $R_{10}$ is independently H, methyl, or ethyl, provided that at least one $R_{10}$ per molecule is methyl or ethyl, and q is an integer of from 1 to about 200, for one or more hydroxyl groups of a sorbitan moiety and, optionally, substituting a carboxylic acid ester group according to the formula:

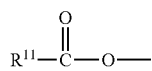

wherein $R^{11}$ is alkyl, alkenyl, or alkynyl, more typically ($C_8$-$C_{24}$) alkyl or ($C_8$-$C_{24}$ alkenyl, for one or more of any remaining hydroxyl groups of the sorbitan moiety and include, for example, propoxylated (2) sorbitan ester, propoxylated (10) sorbitan ester, butoxylated (10) sorbitan ester, propoxylated (20) sorbitan ester, propoxylated (12) sorbitan oleate, propoxylated (20) sorbitan laurate, propoxylated (15) sorbitan cocoate, propoxylated (15) sorbitan cocoate, propoxylated (25) sorbitan diisostearate, propoxylated (8) sorbitan trioleate.

Typically, greater than 30%, more typically greater than 50%, still more typically greater than 80%, and most typically greater than 99% of the $R^{11}$ groups per molecule are each independently methyl or ethyl, based on the total number of moles of $R^{11}$ groups per molecule. In one embodiment, each $R^{11}$ is independently methyl or ethyl, more typically ethyl.

In one embodiment, the structured surfactant composition of the present invention comprises from greater than 0 to about 20 pbw, more typically from about 0.5 to about 10 pbw, and still more typically from about 0.8 to about 5 pbw, alkoxylated nonionic surfactant.

In one embodiment, the structured surfactant composition comprises from greater than 0 to about 40 pbw, more typically from about 5 to about 30 pbw, and still more typically from about 8 to about 20 pbw, alkoxylated nonionic surfactant per 100 pbw anionic surfactant.

When present in a sufficient amount relative to the amount of water and anionic surfactant components of the composition of the present invention, the alkoxylated nonionic surfactant acts as a structurant, that is, as a compound that, in combination with the water and anionic surfactant, forms a shear-thinning fluid that is capable of suspending water insoluble or partially water soluble components. In one embodiment, the alkoxylated nonionic surfactant is present in an amount relative to the amounts of water and anionic surfactant that is at least effective to, in combination with such water and anionic surfactant, form a shear-thinning fluid that is capable of suspending water insoluble or partially water soluble components.

The structured surfactant composition of the present invention and the surfactant blend of the present invention may optionally further comprise, in addition to the anionic surfactant and alkoxylated nonionic surfactant components of the composition of the present invention, one or more cationic surfactants, one or more additional non-ionic surfactants, one or more electrolytes, one or more amphoteric surfactants, one or more zwitterionic surfactants, or a mixture thereof. In cases where any of such optional components functions as a structurant, each of such components may independently be present in an amount in excess of the minimum amount effective to act as a structurant.

In one embodiment, the surfactant blend of the present invention comprises, based on 100 pbw of the blend, from 3 pbw to 40 pbw, more typically from 5 pbw to 30 pbw, of one or more anionic surfactants, and from greater than 0 pbw to 40 pbw, more typically from 0.5 pbw to 10 pbw, of at least one alkoxylated nonionic surfactant.

Cationic surfactants are known. Any cationic surfactant that is acceptable for use in the intended end use application is suitable as the cationic surfactant component of the composition of the present invention, including, for example, mono-cationic surfactants according to formula (VIII) below:

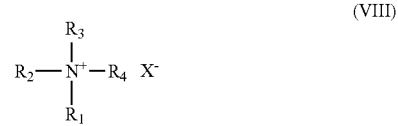

(VIII)

wherein:
$R_1$, $R_2$, $R_3$ and $R_4$, are independently hydrogen, an organic group, provided that at least one of $R_1$, $R_2$, $R_3$ and $R_4$ is not hydrogen.
X is an anion.
If one to three of the R groups are hydrogen, the compound may be referred to as an amine salt. Some examples of cationic amines include polyethoxylated (2) oleyl/stearyl amine, ethoxylated tallow amine, cocoalkylamine, oleylamine, and tallow alkyl amine.

For quaternary ammonium compounds (generally referred to as quats) $R_1$, $R_2$, $R_3$, and $R_4$ may be the same or different organic group, but may not be hydrogen. In one embodiment, $R_1$, $R_2$, $R_3$, and $R_4$ are each ($C_8$-$C_{24}$) branched or linear alkyl, which may comprise additional functionality such as, for example, fatty acids or derivatives thereof, including esters of fatty acids and fatty acids with alkoxylated groups, alkyl amido groups, aromatic rings, heterocyclic rings, phosphate groups, epoxy groups, and hydroxyl groups. The nitrogen atom may also be part of a heterocyclic or aromatic ring system, e.g., cetethyl morpholinium ethosulfate or steapyrium chloride.

Suitable anions include, for example, chloride, bromide, methosulfate, ethosulfate, lactate, saccharinate, acetate or phosphate.

Examples of quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl-dimethyl-(2)hydroxyethyl ammonium dihydrogen phosphate (also known as hydroxyethyl cetyldimonium phosphate), bassuamidopropylkonium chloride, cocotrimonium chloride, distearyldimonium chloride, wheat germ-amidopropalkonium chloride, stearyl octyidimonium methosulfate, isostearaminopropalkonium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate.

Quaternary ammonium compound of the dialkyl amine derivative type distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Electrolytes suitable as an additional structurant component of the composition of the present invention include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and polyelectrolytes, such as uncapped polyacrylates, polymaleates, or polycarboxylates, lignin sulphonates or naphthalene sulphonate formaldehyde copolymers. Electrolytes may be added as a separate component of the structured surfactant or may be added as a part of another component of the composition, e.g., amphoteric surfactants, such as sodium lauroamphoacetate, typically contain an electrolyte, such as sodium chloride.

In one embodiment, the composition comprises, based on 100 pbw of the composition, from about 0.1 pbw to about 15 pbw, more typically from about 1 pbw to about 6 pbw of an electrolyte.

Typically, the greater the amount of anionic surfactant present in relation to its solubility, the lesser the amount of structurant required in order to form a structure capable of supporting solid materials and/or to cause flocculation of the structured surfactant. The structurant is incorporated in an amount sufficient to promote the structured surfactant composition and may be added separately or may be included in one of the other raw materials added to the composition.

In one embodiment, the structured surfactant composition of the present invention comprises, based on 100 pbw of the structured surfactant composition, up to about 40 pbw, more typically from about 0.5 to about 25 pbw and still more typically from about 1 to about 10 pbw of one or more structurants.

Nonionic surfactants are known. Any nonionic surfactant that is acceptable for use in the intended end use application is suitable as the optional nonionic surfactant component of the composition of the present invention, including compounds produced by the condensation of alkylene oxide groups with an organic hydrophobic compound which may be aliphatic or alkyl aromatic in nature. Examples of useful nonionic surfactants include the polyethylene, polypropylene, and polybutylene oxide condensates of alkyl phenols, fatty acid amide surfactants, polyhydroxy fatty acid amide surfactants, amine oxide surfactants, alkyl ethoxylate surfactants, alkanoyl glucose amide surfactants, and alkylpolyglycosides. Specific examples of suitable nonionic surfactants include alkanolamides such as cocamide DEA, cocamide MEA, cocamide MIPA, lauramide DEA, and lauramide MEA, alkyl amine oxides such as lauramine oxide, cocamine oxide, cocamidopropylamine oxide, and lauramidopropylamine oxide, sorbitan laurate, sorbitan distearate, fatty acids or fatty acid esters such as lauric acid, and isostearic acid, fatty alcohols or ethoxylated fatty alcohols such as lauryl alcohol, laureth4, laureth-7, laureth-9, laureth40, trideceth alcohol, C11-15 pareth-9, C12-13 Pareth-3, and C14-15 Pareth-11, alkylpolyglucosides such as decyl glucoside, lauryl glucoside, and coco glucoside.

Zwitterionic surfactants are known. Any Zwitterionic surfactant that is acceptable for use in the intended end use application is suitable as the optional Zwitterionic surfactant component of the composition of the present invention, including, for example, those which can be broadly described as derivatives of aliphatic quaternary ammonium, phosphonium, and sulfonium compounds in which the aliphatic radicals can be straight chain or branched and wherein one of the aliphatic substituents contains from about 8 to 18 carbon atoms and one contains an anionic water-solubilizing group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines.

Amphoteric surfactants are known. Any amphoteric surfactant that is acceptable for use in the intended end use application is suitable as the optional amphoteric surfactant component of the composition of the present invention, including, for example, derivatives of aliphatic secondary and tertiary amines in which the aliphatic radical can be straight chain or branched and wherein one of the aliphatic substituents contains from about 8 to about 18 carbon atoms and one contains an anionic water solubilizing group. Specific examples of suitable amphoteric surfactants include salts, typically alkali metal, alkaline earth metal, ammonium or substituted ammonium salts, of alkyl amphocarboxy glycinates and alkyl amphocarboxypropionates, alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one embodiment, the surfactant component of the present invention may optionally comprise, based on 100 pbw of the total amount of surfactants:

up to about 20 pbw, more typically from about 0.1 to about 10, and still more typically from about 0.5 to about 6, of a cationic surfactant, up to about 20 pbw, more typically from about 0.5 to 10, and still more typically from about 1 to about 6 of a nonionic surfactant, up to about 25 pbw, more typically from about 1 to about 20, and still more typically from about 2 to about 10 of an Zwitterionic or amphoteric surfactant.

The structured surfactant composition of the present invention may optionally further comprise one or more preservatives, such as benzyl alcohol, methyl paraben, propyl paraben, or imidazolidinyl urea, and DMDM hydantoin, and may optionally further comprise one or more pH adjusting agents, such as citric acid, succinic acid, phosphoric acid, sodium hydroxide, or sodium carbonate.

In one embodiment, the composition of the present invention comprises, based on 100 pbw of the composition and inclusive of any surfactant used as a structuring agent, a total amount of from about 0.1 to about 40 pbw, more typically from about 0.5 to about 30 pbw, and still more typically from about 1 to about 15 pbw, of one or more cationic surfactants, nonionic surfactants, amphoteric surfactants, and/or zwitterionic surfactants.

The structured surfactant composition of the present invention may optionally further comprise one or more polymers and/or thickeners, chosen from the groups of clays, substituted or unsubstituted hydrocolloids, acrylate polymers, cationic polymers, hydrohobically modified nonionic polyols, and mixtures thereof. Some examples of clays include bentonite, kaolin, montmorillonite, sodium magnesium silicate, hectorite, magnesium aluminum silicate. Some examples hydrocolloids in the unmodified form include agar, alginate, arabinoxylan, carrageenan, cellulose derivatives, such as carboxyalkyl celluose, hydroxyalkyl cellulose, hydroxyalkyl alkyl cellulose, and alkyl cellulose, curdlan, gelatin, gellan, β-glucan, guar gum, gum arabic, locust bean gum, pectin, starch, succinoglycan, Xanthan gum. Some examples of modified or substituted hydrocolloids are hydroxy methyl cellulose, PG-hydroxyethyl cellulose, quaternary ammonium derivatives of hydroxyethyl cellulose, quaternary ammonium derivatives of guar gum (such as Jaguar C-17, Jaguar C-14S, Jaguar Excel, Jaguar C-162 from Rhodia), hydroxypropyl guars (Jaguar HP-8, Jaguar HP-105, Jaguar HP-60, Jaguar HP-120, Jaguar C-162), modified starches, such as sodium hydroxypropyl starch phosphate (Pure-Gel 980 and Pure-Gel 998 from Grain Processing Corporation), potato starch modified (such as Structure-Solanace from National Starch), acrylate copolymers such as acrylates/aminoacrylates/C10-30 alkyl PEG-20 itaconate copolymer (such as Structure-Plus from National Starch), cationic polymers (such as Rheovis CSP, Rheovis CDE, Rheovis CDP from Ciba), polyacrylimidomethylpropane Sulfonate/Polyquaternium-4 (Plexagel ASC from ISP), hydrohobically modified nonionic polyols (Acusol 880, Acusol 882 from Rohm & Haas), and PEG-150 distearate. In general, personal care compositions may optionally comprise, based on 100 pbw of the personal care composition and independently for each such ingredient, up to about 10 pbw, preferably from 0.5 pbw to about 5.0 pbw, of such other ingredients, depending on the desired properties of the personal care composition.

In one embodiment, the pH of the composition of the present invention is less than 7, more typically within the range of from about 5 to less than 7, more typically, from about 5 to about 6.5. For compositions having a pH of less than 5, the anionic surfactant is typically selected from phosphate surfactants, anionic sulfonate surfactants, and anionic carboxylate surfactants.

In one embodiment, the structured surfactant composition is made by combining and mixing the anionic surfactant, the alkoxylated nonionic surfactant, and water.

In one embodiment, the structured surfactant composition is made by diluting the surfactant blend of the present invention with water.

In one embodiment, an electrolyte is added to the mixture of anionic surfactant, nonionic surfactant and water or to the diluted surfactant blend.

In one embodiment, the pH of the mixture of anionic surfactant, nonionic surfactant and water or of the diluted surfactant blend is adjusted to be less than 7, more typically to be within the range of from about 5 to less than 7, more typically, from about 5 to about 6.5.

In one embodiment, the structured surfactant composition is subjected to mixing as required to form a homogeneous single phase.

In one embodiment, the structured surfactant composition is subjected to a high shear mixing in known high shear mixing equipment, such as, for example, a high shear mixer or a homogenizer.

Shear-thinning viscosity is measured by known viscometric methods, such as for example, using a rotational viscometer, such as a Brookfield viscometer. In one embodiment, the composition of the present invention exhibits shear-thinning behavior when subjected to viscosity measurement using a Brookfield rotational viscometer, equipped with an appropriate spindle, at a rotation speed of from about 0.1 revolutions per minute ("rpm") to about 60 rpm.

The composition of the present invention is capable of suspending water-insoluble particles or partially water soluble components, such as vegetable oils, mineral oils, silicone oils, solid particles, abrasives, and similar articles. The composition provides a means to include otherwise difficult to incorporate components in surfactant mixtures resulting in cosmetic preparations with multi-functional benefits including, in some cases, cleansing, moisturizing, improved skin feel, exfoliation/abrasion, novel appearance, or a combination of these benefits.

The ability of a composition to suspend water insoluble or partially water insoluble components is typically evaluated by mixing the composition with sufficient vigor to entrap air bubbles in the composition and then visually observing whether the air bubbles remain entrapped in the composition for a defined period of time, such as for example, 12 to 24 hours, under defined environmental conditions, such as for example, room temperature. In one embodiment, the composition of the present invention is capable of suspending air bubbles for at least 1 week, and more typically for at least 3 months. A composition that is capable of suspending air bubbles under the for at least 12 hours at room temperature is deemed to be generally capable of suspending water insoluble or partially water soluble components in the composition under generally anticipated processing, storage, and use conditions for such composition. For components other than air, the result of the air suspension test should be confirmed by conducting an analogous suspension test using the component of interest. For unusually rigorous processing, storage and/or use conditions, more rigorous testing may be appropriate.

In one embodiment, the ability to suspend water insoluble or partially water insoluble components is evaluated under more rigorous conditions, that is, the mixed samples are visually evaluated after subjecting the samples to one or more freeze/thaw cycles, wherein each freeze/thaw cycle consists of 12 hours at −10° C. and 12 hours at 25° C. In one embodiment, composition of the present invention remains capable of suspending air bubbles after one freeze/thaw cycle, more typically after 3 freeze/thaw cycles.

In one embodiment, the composition of the present invention further comprises one or more water insoluble or partially water soluble components. Such components may be in the form of a solid, a liquid, or a gas and may comprise one or more materials selected from water insoluble or partially water soluble chemically stable benefit agents, such as, for example, in the case of a personal care application, emollients, conditioners, moisturizers, vitamins, vitamin derivatives, anti-UV agents, anti-bacterial agents, anti-fungal agents, tanning accelerators, anti-aging agents, anti-wrinkle agents, antiperspirants, deodorants, essential oils, fragrances, air, or abrasives, and water insoluble or partially water soluble chemically stable appearance modifying additives such as, for example, colored or reflective particles or beads such as particles of mica, titanium dioxide, or glycol stearate.

In one embodiment, the personal care composition of the present invention comprises a structured surfactant component according to the present invention that forms a first "phase" (which may itself comprise a plurality of phases, including aqueous phases, laminar surfactant phases and spherulitic surfactant phases, as discussed above) and the composition further comprises one or more additional phases that are at least substantially distinct from such first phase. As used herein in reference to the phases of a multiphase embodiments of the present invention, the terminology "substantially distinct" means that the phases each exhibit substantially homogeneous properties within a given phase and that the phases differ with respect to at least one characteristic or property, such as for example, visual characteristics, such as color, clarity, pearlescence, or physical/chemical properties, such as viscosity, lubricity, and/or benefit agent content.

In one embodiment, the structured surfactant component forms a first phase and the composition further comprises at least one additional phase that is at least substantially distinct from the first phase wherein each of such phases is a continuous phase and the phases are disposed adjacent to each other.

In one embodiment, the structured surfactant component forms a first phase and the composition further comprises at least one additional phase that is at least substantially distinct from the first phase wherein one of such phases is a continuous phase, the other of such phases is a discontinuous phase, and the discontinuous phase is dispersed within the continuous phase.

In one embodiment, the structured surfactant component forms a first phase and the composition further comprises at least one additional phase wherein that is at least substantially visually distinct from the first phase, such as for example, a composition comprising an opaque water insoluble component suspended in structured surfactant component.

In one embodiment, the structured surfactant component forms a first phase that exhibits shear-thinning viscosity and is capable of suspending water insoluble or partially water soluble components.

In one embodiment, the structured surfactant component forms a first phase, typically a continuous phase, that exhibits shear-thinning viscosity and is capable of suspending water insoluble or partially water soluble components and the composition further comprises at least one additional phase, typically a discontinuous phase, that is at least substantially distinct form the first phase, wherein the additional phase comprises one or more water insoluble or partially water soluble components.

In another embodiment, the structured surfactant component forms a first phase that exhibits shear-thinning viscosity and is capable of suspending water insoluble or partially water soluble components and the composition further comprises at least one additional phase, such as a second structured surfactant component, that is at least substantially distinct from the first phase and that exhibits shear-thinning viscosity and is capable of suspending water insoluble or partially water soluble components.

In one embodiment, the composition of the present invention comprises two distinct phases, wherein each of the phases is a continuous phase and the phases are disposed adjacent to each other.

In one embodiment, the composition of the present invention comprises two distinct phases, wherein one phase is a continuous phase, the other phase is a discontinuous phase, and the discontinuous phase is adjacent to or dispersed within the continuous phase.

In one embodiment, the composition of the present invention comprises two distinct phases, wherein each phase is a continuous phase and the two phases are disposed in a mutually interpenetrating network.

In one embodiment, a personal care composition of the present invention comprises two or more visually distinct phases. In one embodiment, the two or more visually distinct phases exhibit a visual appearance of alternating stripes.

The composition of the present invention is useful in, for example, personal care applications, such as shampoos, body wash, hand soap, lotions, creams, conditioners, shaving products, facial washes, neutralizing shampoos, personal wipes, and skin treatments, and in home care applications, such as liquid detergents, laundry detergents, hard surface cleansers, dish wash liquids, toilet bowl cleaners, as well as other applications, such as oil field and agrochemical applications.

In one embodiment, the composition of the present invention is a personal care composition.

In one embodiment, the personal care composition of the present invention comprises a structured surfactant composition of the present invention in combination with additional water and/or one or more additional ingredients and suitable personal care compositions are made by diluting the structured surfactant composition with water and/or mixing the structured surfactant composition with additional ingredients.

In one embodiment, the personal care composition consists essentially of the structured surfactant composition of the present invention, i.e., the structured surfactant composition is simply repackaged as a personal care composition.

In one embodiment, the personal care composition of the present invention further comprises one or more benefit agents, such as emollients, moisturizers, conditioners, skin conditioners, hair conditioners, vitamins or their derivatives, antioxidants, free-radical scavengers, abrasives, dyes, hair coloring agents, bleaching agents, hair bleaching agents, anti-UV agents, UV absorbers, antimicrobial agents, antibacterial agents, antifungal agents, melanin regulators, tanning accelerators, depigmenting agents, skin-coloring agents, liporegulators, weight-reduction agents, anti-acne agents, antiseborrhoeic agents, anti-ageing agents, anti-wrinkle agents, keratolytic agents, anti-inflammatory agents, refreshing agents, cicatrizing agents, vascular-protection agents, antiperspirants, deodorants; immunomodulators, nourishing agents, agents for combating hair loss, reducing agents for permanent-waving, essential oils and fragrances.

In one embodiment, the personal care composition of the present invention further comprises from about 0.1 to about 50 pbw, more typically from about 0.3 to about 25 pbw, and still more typically from about 0.5 to 10 pbw, of one or more benefit agents.

The personal care composition according to the present invention may optionally further comprise other ingredients, such as, for example, preservatives such as benzyl alcohol, methyl paraben, propyl paraben and imidazolidinyl urea, thickeners and viscosity modifiers such as block polymers of ethylene oxide and propylene oxide, electrolytes, such as sodium chloride, sodium sulfate, and polyvinyl alcohol, pH adjusting agents such as citric acid, succinic acid, phosphoric acid, sodium hydroxide, and sodium carbonate, perfumes, dyes, and sequestering agents, such as disodium ethylenediamine tetra-acetate. In general, personal care compositions may optionally comprise, based on 100 pbw of the personal care composition and independently for each such ingredient, up to about 10 pbw, preferably from 0.5 pbw to about 5.0 pbw, of such other ingredients, depending on the desired properties of the personal care composition.

In general, personal care composition of the present invention may optionally comprise, based on 100 pbw of the personal care composition and independently for each such ingredient, up to about 15 pbw, preferably from 0.5 pbw to about 10 pbw, of such other ingredients, depending on the desired properties of the personal care composition.

The personal care composition of the present invention is used in a manner know in the art, for example, in-the case of a cleanser or shampoo, by application of the cleanser or shampoo to the skin and/or hair and optionally rinsing the cleanser or shampoo off of the skin and/or hair with water.

EXAMPLES 1-6 AND COMPARATIVE EXAMPLE C1

The compositions of Examples 1 - 6 and Comparative Example C1 were made by mixing the ingredients to give the relative amounts listed in TABLES I and II below (based on 100 pbw) Typically, this involved using an ingredient that already contained some water and using it in the composition to provide the specified level of active ingredient.

Samples were centrifuged at 20,000 G for 15 min to force the phases to separate and the relative amount of structured phase and non-structured phase was evaluated by visual inspection.

TABLE I

| Components | Comp. Ex. C1 | Ex. 1 | Ex. 2 | Ex. 3 | Ex. 4 |
|---|---|---|---|---|---|
| Sodium Trideceth Sulfate | 11.2 | 10.8 | 10.8 | 10.6 | 10.8 |
| Sodium Lauroamphoacetate | 6.7 | 6.5 | 6.5 | 6.4 | 6.5 |
| Polypropylene glycol-15 Stearyl Ether (Hetoxol SP-15, Global Seven) | — | — | 3.8 | 5.6 | |
| Polypropylene glycol-30 Cetyl Ether (Hetoxol C-30P, Global Seven) | — | 3.8 | — | — | — |
| Propoxylated (20 PO) Sorbitan Monolaurate | — | — | — | — | 3.8 |
| NaCl | 2.0 | 1.9 | 1.9 | 1.9 | 1.9 |
| glydant | 0.3 | 0.3 | 0.3 | 0.3 | 0.3 |
| citric acid | 0.9 | 0.9 | 0.9 | 0.9 | 0.9 |
| water | 78.8 | 75.9 | 75.9 | 74.5 | 75.9 |
| appearance (% cloudy/structured) | 50 | 75 | 85 | 90 | 100 |
| appearance (% clear) | 50 | 25 | 15 | 10 | 0 |

TABLE II

| Components | Ex. 5 | Ex. 6 |
|---|---|---|
| Sodium Trideceth Sulfate | 12.3 | 8.5 |
| Sodium Lauroamphoacetate | 14.5 | 10.0 |
| Polypropylene glycol-15 Stearyl Ether (Hetoxol SP-15, Global Seven) | 3.2 | 2.2 |
| Trideceth (3) Carboxylic Acid | | 5.7 |
| glydant | 0.3 | 0.4 |
| citric acid | 0.6 | 1.5 |
| water | 69.1 | 71.7 |
| appearance (% cloudy/structured) | 100 | 100 |
| appearance (% clear) | 0 | 0 |

Structured liquid compositions containing an anionic surfactant and a propoxylated alcohol nonionic surfactant (Hetoxol SP-15 (propoxylated (15) stearyl alcohol) or Hetoxol C-30P propoxylated (30) cetyl alcohol)) shows an increase in the "structured" phase.

EXAMPLES 7 & 8 AND COMPARATIVE EXAMPLES C2, C3, AND C4

The compositions of Example 7 and Comparative Example C2 were made by mixing the ingredients to give the relative amounts listed in TABLE III (based on 100 pbw). Typically, this involved using an ingredient that already contained some water and using it in the composition to provide the specified level of active ingredient.

Example 7, Comparative Examples C2, and a Sodium Lauryl Sulfate standard were then diluted to contain exactly 5% active surfactants, creating Example 8 and Comparative Examples C3 and C4. The exact ratios of surfactant are given in TABLE IV below.

The compositions were each subjected to Zein testing as follows. A 5% aqueous solution of each composition to be tested was made. A 5% aqueous solution of sodium lauryl sulfate (SLS) was also made, to be used as the negative control. 4 grams of Zein protein were mixed into 40 grams of each of the 5% solutions. The mixtures were agitated at room temperature for 24 hours with continual shaking. The mixtures were then filtered using a syringe filter assembly fitted with a 0.45 μm Nylon membrane. The filtrate was diluted by dissolving 0.1 grams of filtrate in 10 grams of a 2% SLS solution. The absorbance at a wavelength ("λ") of 278 nm was determined for each of the diluted filtrate samples using a UV-Vis spectrophotometer (Varian Carimed) in the range of 200 nm<λ<350 nm at a scanning rate of 800 nm/min. The 2% SLS solution is used as blank for UV test. The concentration of dissolved Zein protein in each diluted filtrate sample was determined from an absorbance versus concentration calibration curve that had been generated based on measurements of absorbance at λ=278 nm for a series of samples of known dissolved Zein protein concentration. Results are reported in TABLE IV below as dissolved Zein protein concentration as grams protein per milliLiter of solution ("g/mL"). Higher dissolved Zein protein concentration indicates higher risk of eye and/or skin irritation.

The results of the Zein testing show that including the PPG-15 stearyl ether in a composition (and keeping the ratios of the other surfactants the same), reduces the risk that the composition will irritate the eyes and/or skin.

TABLE III

| Components | Comp. Ex. C2 | Ex. 7 |
|---|---|---|
| Sodium Trideceth Sulfate | 11.0 | 10.4 |
| Sodium Lauroamphoacetate | 6.6 | 6.3 |
| PPG-15 Stearyl Ether | — | 5.6 |
| NaCl | 2.0 | 1.9 |
| glydant | 0.3 | 0.3 |
| citric acid | 1.1 | 1.0 |
| water | 79.0 | 73.5 |

TABLE IV

| Components | Comp. Ex. C3 | Comp. Ex. C4 | Ex. 8 |
|---|---|---|---|
| Sodium Lauryl Sulfate | 5 | | |
| Sodium Trideceth Sulfate | | 3.1 | 2.3 |
| Sodium Lauroamphoacetate | | 1.9 | 1.4 |
| PPG-15 Stearyl Ether | | — | 1.3 |
| Zein Number (g/mL) | 0.1436 | 0.0607 | 0.0481 |

The invention claimed is:

1. An aqueous structured surfactant composition, comprising water, one or more anionic surfactants, at least one zwitterionic surfactant or amphoteric surfactant, and at least one, propoxlated alcohol according to formula (II):

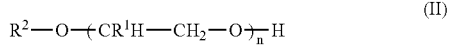

(II)

wherein
R¹ is methyl,
R² is (C$_{12}$-C$_{20}$)alkyl, and
n is an integer of from about 4 to about 30,
said composition comprising at least one lamellar surfactant phase and exhibiting shear-thinning viscosity and is capable of suspending water insoluble or partially water soluble components.

2. The composition of claim 1, wherein the composition comprises, based on 100 parts by weight of the composition, from 3 parts by weight to 40 parts by weight of one or more anionic surfactants and from greater than 0 parts by weight to 40 parts by weight of the at least one propoxylated alcohol.

3. The composition of claim 1, wherein the one or more anionic surfactants comprise one or more of sodium trideceth sulfate, sodium tridecyl sulfate, ammonium trideceth sulfate, ammonium tridecyl sulfate, sodium trideceth carboxylate.

4. The composition of claim 1, wherein the at least one propoxylated alcohol comprises polypropylene glycol-30 cetyl ether, polypropylene glycol-15 stearyl ether or a mixture thereof.

5. The composition of claim 1, wherein the composition further comprises, based on 100 parts by weight of the composition, from about 0.1 part by weight to about 15 parts by weight of an electrolyte.

6. The composition of claim 1, further comprising an electrolyte selected from alkali metal halides, ammonium halides, and mixtures thereof.

7. The composition of claim 1, wherein the composition further comprises, based on 100 parts by weight of the composition, from about 0.1 part by weight to about 10 parts by weight of a cationic surfactant.

8. The composition of claim 1, further comprising a cationic surfactant selected from amine salts, quatemary ammonium compounds, and mixtures thereof.

9. The composition of claim 1, wherein the composition further comprises, based on 100 parts by weight of the composition, from about 0.5 part by weight to 10 parts by weight of a nonionic surfactant in addition to the at least one propoxylated alcohol.

10. The composition of claim 1, further comprising a nonionic surfactant in addition to the at least one propoxylated alcohol, selected from alkanolamides, alkyl amine oxides, fatty acids or fatty acid esters, fatty alcohols or ethoxylated fatty alcohols, alkylpolyglucosides, and mixtures thereof.

11. The composition of claim 1, wherein the composition comprises based on 100 parts by weight of the composition, from about 1 part by weight to about 20 parts by weight of the Zwitterionic or amphoteric surfactant.

12. The composition of claim 1, wherein the composition comprises an amphoteric surfactant selected from salts of cocoamphoacetate, cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, stearoamphoacetate, and mixtures thereof.

13. A surfactant blend, comprising, based on 100 parts by weight of the blend, from 3 parts by weight to 40 parts by weight of one or more anionic surfactants, from about 1 parts by weight to about 20 parts by weight or at least one zwitterionic surfactant or amphoteric surfactant, from about 0.1 pbw to about 15 pbw of an electrolyte, and from greater than 0 parts by weight to 40 parts by weight of at least one propoxylated alcohol according to formula (II):

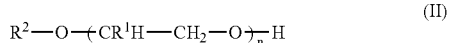

(II)

wherein
R¹ is methyl,
R² is (C$_{12}$-C$_{20}$)alkyl, and
n is an interger of from about 4 to about 30.

14. A personal care composition comprising water, one or more anionic surfactants, at least one zwitterionic surfactant or amphoteric surfactant, and at least one propoxylated alcohol according to formula (II):

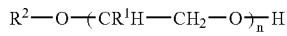
(II)

wherein
R¹ is methyl,
R² is (C$_{12}$-C$_{20}$)alkyl, and
n is an interger of from about 4 to about 30
said composition comprising at least one lamellar sufactant phase and exhhibiting shear-thinning viscosity and is capable of suspending water insoluble or partially water soluble components.

15. The composition of claim 14, further comprising one or more benefit agents selected from emollients, moisturizers, conditioners, skin conditioners, hair conditioners, vitamins or their derivatives, antioxidants, free-radical scavengers, abrasives, dyes, hair coloring agents, bleaching agents, hair bleaching agents, anti-UV agents, UV absorbers, antimicrobial agents, antibacterial agents, antifungal agents, melanin regulators, tanning accelerators, depigmenting agents, skin-coloring agents, liporegulators, weight-reduction agents, anti-acne agents, antiseborrhoeic agents, anti-ageing agents, anti-wrinkle agents, keratolytic agents, anti-inflammatory agents, refreshing agents, cicatrizing agents, vascular-protection agents, antiperspirants, deodorants, immunomodulators, nourishing agents, agents for combating hair loss, reducing agents for permanent-waving, essential oils, fragrances, and mixtures thereof.

16. The composition of claim 14, further comprising one or more polymers and/or thickeners, selected from clays, substituted or unsubstituted hydrocolloids, acrylate polymers, cationic polymers, hydrohobically modified nonionic polyols, and mixtures thereof.

17. The composition of claim 14, further comprising one or more water insoluble or partially water soluble components.

18. An aqueous composition, comprising, based on 100 parts by weight of the composition:
   from about 3 to about 40 pbw of an anionic surfactant selected from sodium trideceth sulfate, sodium tridecyl sulfate, and mixtures thereof,
   from greater than 0 parts by weight to 40 parts by weight of a propoxylated alcohol selected from polypropylene glycol-30 cetyl ether, polypropylene glycol-15 stearyl ether, and mixtures thereof,
   from about 1 part by weight to about 20 parts by weight of an amphoteric surfactant selected from salts of cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, stearoamphoacetate, and mixtures thereof, and
   from about 0.1 pbw to about 15 pbw of an electrolyte, wherein the composition comprises at least one lamellar sufactant phase.

* * * * *